United States Patent [19]
Dill et al.

[11] 4,204,037
[45] May 20, 1980

[54] METHOD AND AUTOMATED APPARATUS FOR DETECTING COLIFORM ORGANISMS

[76] Inventors: Robert A. Frosch, Administrator of the National Aeronautics and Space Administration, with respect to an invention of W. Preston Dill, Houston, Tex.; Rueben E. Taylor, Seabrook, Tex.; Eldon L. Jeffers, La Porte, Tex.

[21] Appl. No.: 893,657

[22] Filed: Apr. 4, 1978

[51] Int. Cl.² .................. C12Q 3/00; C12Q 1/06; C12M 1/36
[52] U.S. Cl. .................... 435/3; 23/230 B; 204/195 B; 422/68; 435/32; 435/34; 435/38; 435/39; 435/289; 435/290; 435/291; 435/311; 435/316
[58] Field of Search ............... 195/103.5 R, 103.5 M, 195/127, 139; 422/68; 23/230 B; 204/195 B, 1 E; 435/3, 32, 34, 38, 39, 289, 290, 291, 296, 299, 311, 316; 364/496

[56] References Cited
U.S. PATENT DOCUMENTS

| | | | |
|---|---|---|---|
| 3,421,982 | 1/1969 | Schultz et al. | 195/127 X |
| 3,743,581 | 7/1973 | Cady et al. | 195/103.5 R |
| 4,009,078 | 2/1977 | Wilkins et al. | 195/103.5 R |
| 4,030,979 | 6/1977 | Zuber | 195/103.5 M |
| 4,149,938 | 4/1979 | Young et al. | 195/127 |

*Primary Examiner*—Robert J. Warden
*Attorney, Agent, or Firm*—Marvin J. Marnock; John R. Manning; Marvin F. Matthews

[57] ABSTRACT

Method and automated apparatus are disclosed for determining the time of detection of metabolically produced hydrogen by coliform bacteria cultured in an electroanalytical cell from the time the cell is inoculated with the bacteria. The detection time data provides bacteria concentration values. The apparatus is sequenced and controlled by a digital computer to discharge a spent sample, clean and sterilize the culture cell, provide a bacteria nutrient into the cell, control the temperature of the nutrient, inoculate the nutrient with a bacteria sample, measures the electrical potential difference produced by the cell and measures the time of detection from inoculation.

11 Claims, 5 Drawing Figures

METHOD AND AUTOMATED APPARATUS FOR DETECTING COLIFORM ORGANISMS

ORIGIN OF THE INVENTION

The invention described herein was made in the performance of work under a NASA contract and is subject to the provisions of Section 305 of the National Aeronautics and Space Act of 1958, public 85-568 (72 Stat. 435; 42 U.S.C. 2457).

BACKGROUND OF THE INVENTION

1. Field of the Invention

The present invention generally relates to methods and apparatus for automatically making periodic quantitative determinations of bacteria present in water. More particularly, the invention relates to method and apparatus for automatically making periodic quantitative determinations of coliform organisms present in water such as waste water, effluent or fresh water by using electrochemical techniques based on detection of metabolic hydrogen liberated by the coliform organisms utilizing changes in electrode potentials.

2. Description of the Prior Art

Detection and quantitative measurement of the number of coliform bacteria present in water is frequently of vital importance for determining the effectiveness of water treatment processes in removing bacterial contamination. The predominance in sewage of coliform bacteria make this organism a sensitive indicator of pollution. Water is an unfavorable environment for bacteria and those that find their way into water gradually die off. Coliform, along with other bacteria, are also quite readily removed from water by conventional water purification processes. The common intestinal bacteria pathogens are at least as susceptible to the artificial and natural purification processes to which water is subjected as is a more common coliform bacteria. Therefore, the coliform group may be employed as a good indicator of pollution.

Presently, several methods are known for the detection of coliform bacteria in aqueous solutions. These methods are generally divided into two classes of detection, both being based on the production of metabolic hydrogen liberated by the coliform organisms after innoculation into a lactose-containing nutrient broth. However, the prior art techniques developed heretofore are generally time consuming and complex since the techniques involve laboratory procedures which require continual intervention by trained personnel.

One such technique for the quantitative determination of coliform bacteria in an aqueous sample is to position the culture to be tested inside a hermetically sealed chamber and thereafter to measure the increase in pressure due to the metabolically produced hydrogen. For example, Wilkins et al, U.S. Pat. No. 3,907,646, utilizes a differential pressure transducer fitted to a metal cap machined to hermetically seal a conventional test tube. The inlet tube of the transducer is inserted through the cap and soldered into place. The culture to be tested is positioned inside the test tube and the tube and transducer assembly placed within the incubator with the electric output of the transducer being connected to a measuring device. As hydrogen is evolved during the growth cycle of the coliform bacteria, the pressure on the interior of the test tube increases, resulting in a measurable output from the pressure transducer.

The second technique is directed to measuring an increase in voltage in the negative (cathodic) direction resulting from the metabolically induced hydrogen. The increase in electrical potential is measured by a system utilizing two electrodes. For example, Wilkins et al, U.S. Pat. No. 4,009,078, utilizes a test tube containing two electrodes positioned in a growth nutrient broth containing coliform organisms, which is then positioned in a 35° C. water bath. Hydrogen evolution was measured by an increase in voltage in a negative direction caused by metabolic hydrogen production induced by the growth of the bacteria in the culture. As the induced hydrogen increased, the potential difference increased, and with the outputs of the electrodes connected to a suitable measuring device, the increase in potential difference becomes measurable.

Both of the above-described coliform bacteria detection methods utilize a laboratory test tube as the culture cell. While these laboratory methods provide for a rapid determination that bacteria are present in an aqueous sample, they still require constant supervision and intervention by trained personnel to perform the test and are time consuming.

The present invention overcome the deficiencies of the prior art by providing methods and apparatus for automatically and periodically measuring the concentration of coliform bacteria present in a given sample by apparatus which is interfaced with, and controlled by a digital computer enabling the apparatus to provide the desired concentration measurement on a periodic or continuous basis.

SUMMARY OF THE INVENTION

The present invention provides a method and apparatus for automatically and rapidly determining the concentration of coliform bacteria contained in an aqueous sample. This data, when simultaneously available with data from resulting determinations of other parameters, will give a useful picture of the quality of an aqueous sample, and in particular, the effects of various aspects of treatment of the water from which the sample has been taken. In addition, the data will be useful in determining the suitability for discharge of the treated water. According to one embodiment of the present invention, an aqueous sample is periodically obtained from various locations in a water treatment system. The sample is then cultured in a growth medium solution and the electrical potential change between a reference electrode and a measurement electrode, resulting from the metabolically produced hydrogen during the growth cycle of the bacteria, is measured as well as the time of detection of the production of hydrogen from the time of innoculation of the growth medium solution with the bacteria. From such data, the concentration of bacteria in the culture can be determined. Total coliform concentration and fecal coliform concentration can be determined by maintaining the temperature of the innoculated growth medium solution at selected incubation temperatures peculiar to the coliform measurement desired. Means are provided for discharging the culture, cleaning and sterilizing the growth cell after each measurement.

A completely automated electrochemical measuring apparatus which is transportable, accurate and fully reliable, is provided. The apparatus is operated and controlled by an interconnected digital computer in a sequence which activates electrically operated solenoid valves to provide for culturing the aqueous sample to be analyzed, measuring the potential difference produced by the metabolically induced hydrogen, discharging the sample and cleaning and sterilizing the environment in preparation for repeating the cycle. The nutrient growth medium required for analysis of the sample is self-contained within the system. Also self-contained within the system are all of the pumps and valves necessary for automated operation of the measurement system, as well as a plurality of growth cells which may be sequentially cultured to provide for a continuous measuring capability.

The data handling interface to a digital computer is also included in the system for receiving and processing electrical command signals produced by the computer controlling the operation of the system, and for providing test data from the measurement equipment to the computer.

Accordingly, it is a feature of the present invention to provide an automated method and apparatus to determine the presence of coliform bacteria in an aqueous environment.

Another feature of the present invention is to provide an automated method and apparatus to quantitatively determine the concentration of coliform bacteria in an aqueous sample.

Yet another feature of the present invention is to provide an automated method and apparatus to quantitatively determine the concentration of both total coliform and fecal coliform bacteria contained within aqueous solutions.

A still further feature of the invention is to provide automated method and apparatus for quantitatively determining the concentration of coliform bacteria in aqueous sample utilizing a measurement of the differing potential caused by metabolically induced hydrogen.

Another feature of the invention is to provide automated method and apparatus for discharging the bacteria culture and cleaning and sterilizing the bacteria growth cell after each concentration measurement.

These and other features and advantages of the present invention will become apparent from the following detailed description when considered in conjunction with the accompanying drawings.

BRIEF DESCRIPTION OF THE DRAWINGS

In order that the manner in which the above-recited advantages and features of the invention are attained can be understood in detail, a more particular description of the invention may be had by reference to specific embodiments thereof which are illustrated in the appended drawings, which drawings form a part of this specification. It is to be noted, however, that the appended drawings illustrate only typical embodiments of the invention and therefore are not to be considered limiting of its scope when the invention may admit to further equally effective embodiments.

In the drawings.

DETAILED DESCRIPTION OF THE PREFERRED EMBODIMENT

Figure 1:
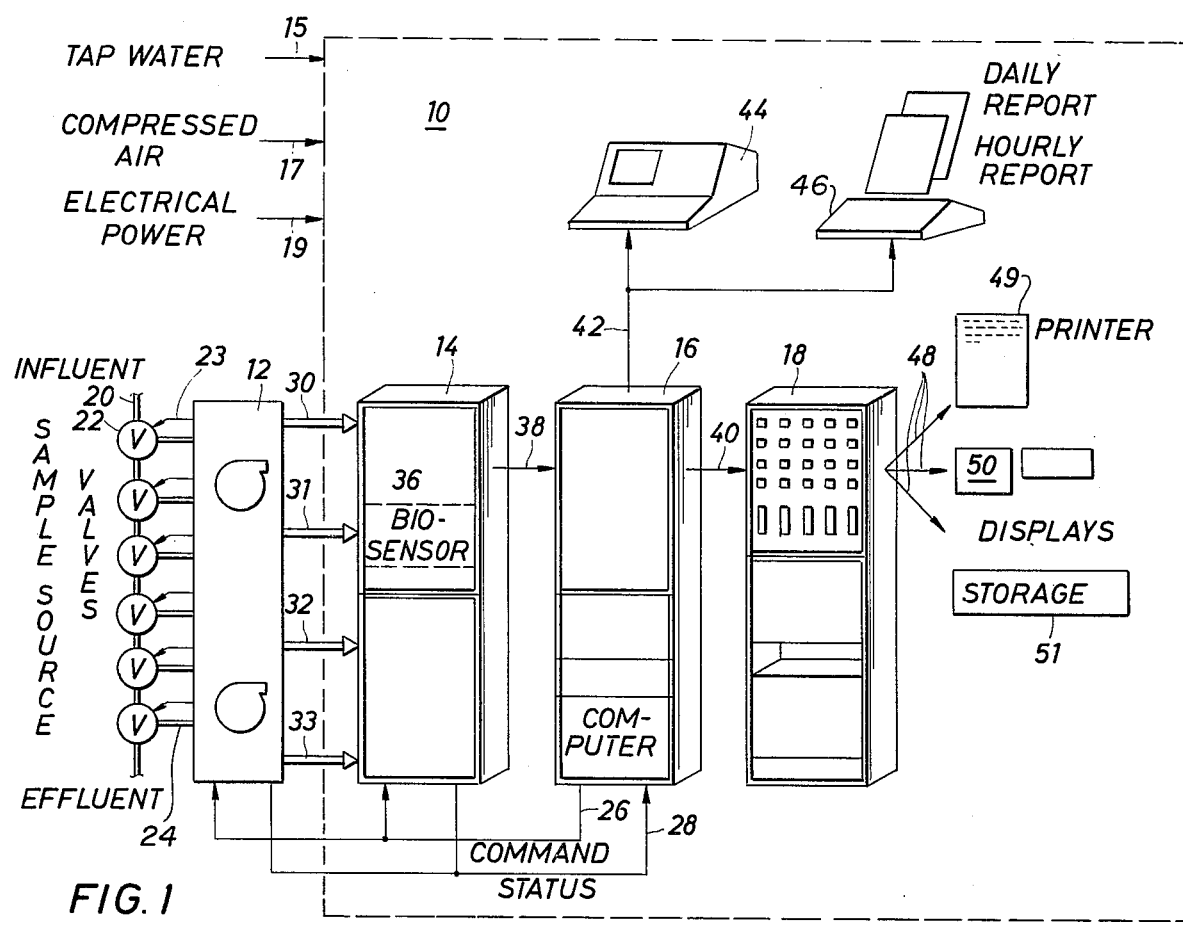
FIG. 1 is a pictorial/block diagrammatic representation disclosing the various assemblies making up a portable water monitoring system of which the present invention forms an important sub-assembly.

Referring now to FIG. 1, an automated water monitoring system 10 incorporating the present invention is shown. The water monitoring system 10 includes an input water sample collection and distribution assembly 12 interconnected to one or more remotely located water sampling locations, such as valves 22, by tubes 24. System 10 also includes an analyzing sensor assembly 14, which comprises various analyzing sub-assemblies useful in determining the chemistry of aqueous solutions, and in addition, the biological quality of the samples taken from the various remote sampling locations along the process flow path in a water treatment system.

Adjacent the analyzing sensor assembly 14, is located a digital computer 16 which provides process and sequencing control signals for automated testing of the water samples and which receives the data signals from the various analyzers of assembly 14. Use of the digital computer 16 allows the water monitoring system 10 to be completely automated, enabling operation of the system with a minimum of personnel.

Also included in the water monitoring system 10 is an analog data acquisition assembly 18, designed to receive analog voltage signals representative of the various water quality parameters and to convert the analog signals into visible engineering unit displays. A signal cable comprising a plurality of conductors 23 provides signal paths from sample collection and distribution assembly 12 to the valve solenoids for operation of valves 22 at the remote water sampling locations 20.

Input connections 15, 17 and 19 are provided for deionized water, compressed air and electrical power, respectively, for use in system 10. Of course, in remote locations or where the water, compressed air or electrical power is not available, suitable sources contained within system 10 may be provided.

Water monitoring system 10 is designed for mounting in a typical instrumentation trailer (not shown). When mounted in such a trailer, system 10 is readily transportable to any desired location for monitoring the quality of water at that location. Suitable locations, for example, could be a sewage treatment plant, industrial effluent discharge, or other locations where permanent water quality monitoring systems are not feasible or justified.

When water monitoring system 10 is positioned adjacent the desired facility, such as a waste water treatment plant (not shown), a plurality of solenoid-operated valves 22 are positioned in the water treatment flow path 20 to allow the collection of a sample at various points along flow path 20. As described above, the sample collection points, including valves 22, may be remote from sample collection and distribution assembly 12.

Sample collection valves 22 are energized in response to signals received from sample collection and distribution assembly 12 over conductors 23, with the sample collection and distribution assembly 12 being, in turn, controlled by commands from the digital computer 16 over conductor 26, the command interface line. Additionally, status signals representing the "on-off" condition of valves 22 are transmitted to the digital computer 16 over conductor 28, the status interface line.

As a valve 22 is energized, a pump within sample collection and distribution assembly 12 is simultaneously activated, drawing a water sample from the flow path 20, through valve 22 and pipes or tubing 24 into the distribution assembly 12. The sample may then be processed by filters (not shown) internal to the sample collection and distribution assembly 12 in response to commands from digital computer 16. As hereinabove described, deionized water, compressed air, and electrical power may be supplied to system 10 through connections 15, 17 and 19, respectively.

Dependent upon the measurement desired, sample collection and distribution assembly 12 can provide the various analyzers and sensor assembly 14 with an unfiltered sample from valves 22 over conduits 30 or 32 or with a filtered sample from one of the valves 22 over conduits 31 or 33. Water samples brought into the analyzing sensor assembly 14 over conduits 30-33 are routed through the various water chemistry and biological detection devices (not shown) within the biosensor assembly 36. The biosensor analyzer assembly 36 includes chemiluminescent and bioluminescent assay subassemblies (not shown) and a coliform detector subassembly 62 (see FIG. 5). The coliform detector subassembly 62 which forms the subject matter of the present invention will be hereinafter further described in greater detail.

As the various analyzers contained within analyzing sensor assembly 14 perform their various functions, the data is collected and transmitted over a sensor/computor data interface, provided by a conductor 38, to the digital computer 16 for processing. Process data may then be coupled through a digital to analog convertor (not shown) and then to the analog data acquisition assembly 18 over a data interface provided by cable 40 where the data is transformed into visual indications of the measurements in an engineering units display. Additionally, the processed digital data may be transmitted over an interface cable 42 to provide displays on a cathode rate tube terminal (C.R.T.) 44 or to provide printouts from a teletype printer 46. Data may also be transmitted over an interface cable 48 to various terminal equipment such as a printer 49, or a display device 50 for providing a visual display, or to a recording device 51 for storage and later retrieval.

Prior to describing in great detail the apparatus comprising the present invention, it may be helpful to describe in simpler terms the hydrogen detection process which the apparatus of the present invention utilizes. The detection technique herein utilized is based on the principle that coliform bacteria characteristically evolve hydrogen gas during the metabolism of the disaccharide lactose.

Figure 2:
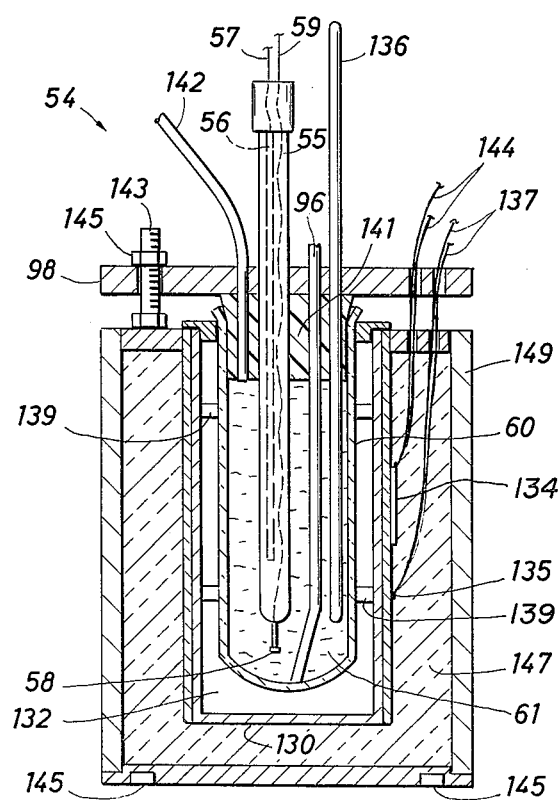
FIG. 2 is an exploded view of the electroanalytical growth cell and measuring electrodes forming the electrical potential measuring sub-assembly of this invention.
Figure 3:
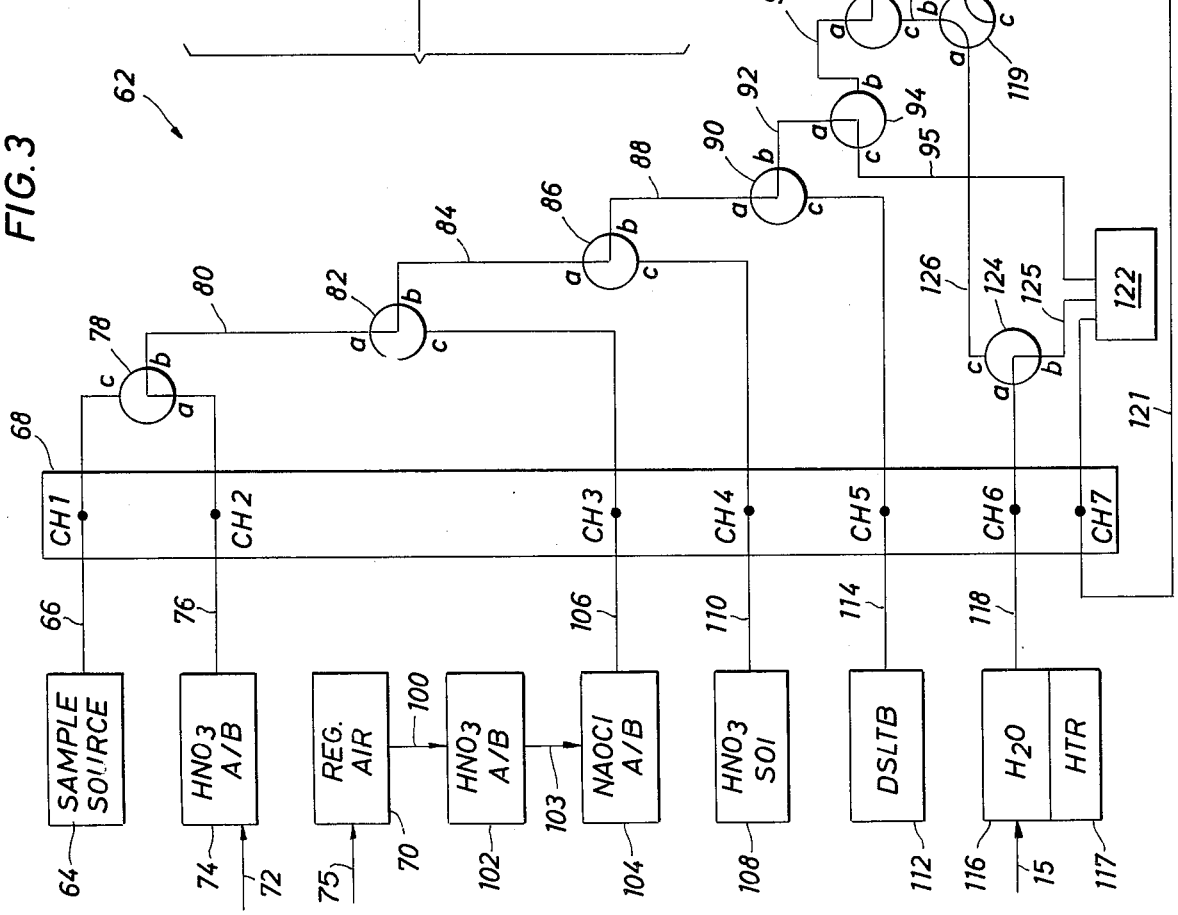
FIG. 3 is a simplified block diagram illustrating a single cell embodiment of the automated coliform detection sub-assembly of the present invention.

Referring now to FIGS. 2 and 3, there is shown an electroanalytical cell 54 used in the embodiments herein described. Cell 54 includes a shell 130 which supports an oil bath 132. Shell 130 is wrapped along the sides and the lower end with a conventional insulating material 147. The insulated shell is then positioned in an open-ended casing 149.

A growth cell 60, preferably a glass test tube, is positioned in oil bath 132 and a pliable stopper 141 is inserted into the open end of growth cell 60 and held in place by a retainer plate 98. Plate 98 is in turn held in place by the use of threaded rods 143 and mating nuts 145 as shown in detail in FIG. 2.

A conventional resistance heater 134 is bonded to the exterior of shell 130 with a pair of electrical power leads 144 connecting heater 134 to a temperature controller 146. Controller 146 receives electrical signals over conductors 137 from a thermistor 135 attached to heater 134. The electrical control signals generated by thermistor 135 control electrical power supplied to heater 134 by controller 146.

To prevent damage to the glass envelope of growth cell 60, a plurality of spacers 139 are provided and positioned between the exterior of cell 60 and the interior of shell 130 to hold the glass envelope in spaced-apart relation to shell 130 within oil bath 132.

A platinum-tipped combination type electrode 55 is interposed through stopper 141 and retainer plate 98 to position the platinum measuring electrode tip 58 on the interior of cell 60. A standard Calomel electrode 56 is centrally enclosed within combination electrode 55. Additionally, a 1/5° thermometer 136 is interposed through stopper 141 and plate 98.

Electrical conductors 57 and 59 connect the SCE and measuring electrodes, respectively, of combination electrode 55 to a high impedance signal conditioner 138 (see FIG. 3), and electrical conductors 137 and 144 connect the thermistor 135 and the heater 134, respectively, to a temperature controller 146 (see FIG. 3). Additionally, a tubing 96 extends through plate 98 to communicate with the lower portion of the interior of cell 60 for admitting and removing nutrient material, bacteria, cleaning and sterilizing agents. In addition, the cell is vented to an overboard drain through a vent tube 142 interposed through stopper 141 and plate 98 to position the extremity flush with the bottom of stopper 141.

When the above-mentioned components, electrodes and thermometer have been positioned through the plate 98, each passage is sealed. Afterwards, the plate 98 is tightened against stopper 141 forcing the stopper into sealing engagement with the upper extremity of cell 60 to prevent a direct communication between oil bath 132 and the interior of cell 60.

In utilizing cell 54, any culture medium which is commonly used for the growth of microorganisms or bacteria can be used, and therefore, the type of culture medium used is not critical. In the present invention, autoclaved double strength lauryl tryptose broth (DSLTB) has been found a suitable nutrient medium and, therefore, was used as the growth medium in the preferred embodiment. The DSLTB 61 is introduced into cell 60 through tubing 96. A sample of the bacteria is also introduced into the growth medium 61 through tubing 96. The temperatures over which the bacteria are grown and eventually detected extend over the range of 15° C. to 60° C. In the present invention, it has been found that the total coliform content can be detected using a controlled temperature of 35° C. and the fecal coliform content of the sample can be detected using a controlled temperature of 44.5° C. Use of the above-mentioned temperatures is based on the minimum detectable limits of the various bacteria cultured. If a sample containing a mixture of two or more types or species of bacteria is cultured within the electroanalytical cell, the bacteria which reaches its minimum detectable limit first is the one which will be detected by the system. Thus, in order to detect coliform bacteria, the temperature is stabilized at 35° C. so that bacteria, other than the coliform bacteria, having a lower minimum detectable limit would be destroyed by the heat, allowing the coliform bacteria to be the first bacteria detected. Similarly, stabilizing the temperature at 44.5° C. will destroy all bacteria, including that coliform bacteria having a lower minimum detectable limit than the fecal coliform bacteria. This will enable the system to detect only fecal coliform bacteria. In electroanalytical cell 54, the temperature is controlled by the heating element 134 submerged in oil bath 132 and heating the oil bath to a predetermined temperature to precisely control the bacteria growth temperature of the nutrient DSLTB 61 within cell 60. The thermometer 136 measures the temperature of the DSLTB 61 and appropriate temperature signals are sent to a heating element control means 146 (see FIG. 3) for controlling the temperature within the selected limits.

In the selected environment growth of the bacteria occurs and once the population level reaches a minimum limit, normally about $5 \times 10^4$ to $5 \times 10^5$ cells, the bacteria can be detected by the change in potential difference created by the metabolic production of hydrogen. The potential always changes in a negative direction, because a change in the bacteria is more negative than that on the measurement electrode. As is common to microorganisms in an electroanalytical cell, the bacteria migrate toward the measuring electrode 58 and their released hydrogen tends to also concentrate about the measuring electrode 58. The presence of hydrogen at the measuring electrode 58 substantially amplifies the characteristics of the electrode such that it becomes similar to the well-known conventional hydrogen electrode. Thus, in effect, a completely different type of measuring electrode is used for the measurement of hydrogen producing organisms than is used for measuring non-hydrogen producing organisms.

The principle behind the operation of the hydrogen electrode is that the following equilibrium exists at the surface of the measuring electrode 58, usually platinum or gold:

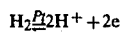

It is clear from this expression that an equilibrium exists between molecular hydrogen and the hydrogen ions in solution and it is the variations within the equilibrium that determines the potential of the electrode. Once an equilibrium has been established at the electrode surface, the electrode is termed a "non-polarizable" or reference electrode. The normal hydrogen (reference) electrode (NHE) is platinum in an acid solution of pH=0 with a saturated solution of molecular hydrogen. The normal hydrogen electrode (NHE) is defined to have a potential of 0.00 volts and forms a relative basis for the potential scale of all other electrode reactions as well as establishes the basis for the electromotive series of metals.

In a more specific aspect to the measurement of hydrogen producing bacteria, a standard Calomel electrode 56 ($Hg$—$Hg_2Cl_2$) positioned on the interior of combination electrode 55, is used as the reference electrode in combination with a metal measuring electrode 58. The Calomel electrode 56 has a potential of about +0.23 volts with respect to the NHE and since the growth medium 61 has a pH of about neutral or 7.0, the measuring hydrogen electrode 58 has a potential of about −0.42 volts with respect to the NHE. Thus, the measuring electrode 58 for hydrogen producing bacteria has a potential of about −0.65 volts, that is, (−0.42)−(+0.23)=−0.65 in a negative direction relative to the Calomel reference electrode 56. Because, in reality a pressure of one atmosphere of hydrogen is never achieved at the measuring electrode because of atmospheric dilution effects due to $CO_2$, nitrogen and the like, a leveling-off of approximately −0.4 to −0.5 volts versus the Calomel reference is achieved in the measurements obtained for hydrogen producing bacteria.

Referring now to FIG. 3, apparatus using one electroanalytical cell 54 for performing the coliform detection of the present invention is shown generally at 62. A sample source reservoir 64 is interconnected to a flexible tubing 66 which forms one channel of a peristaltic pump 68, with the remaining extremity of flexible tubing 66 interconnected to port "c" of a solenoid pilot operated valve 78. Port "b" of valve 78 is connected to one extremity of tubing 80 with the remaining extremity of tubing 80 connected to port "a" of solenoid pilot operated valve 82. Port "b" of valve 82 is connected to one end of tubing 84 with the remaining end connected to port "a" of solenoid pilot operated valve 86. Port "b" of solenoid pilot operated valve 86 is connected to a tubing 88 with the remaining extremity connected to port "a" of solenoid pilot operated valve 90. Port "b" of solenoid pilot operated valve 90 is connected to port "a" of solenoid pilot operated valve 94 by tubing 92. Port "b" of valve 94 is connected to port "a" of solenoid pilot operated valve 99 by tubing 97 with the port "b" connected to tubing 96 shown extending into the interior of bacteria growth cell 60 of electroanalytical cell 54 through plate 98, as hereinabove described.

A source of free air 17 is connected by tube 72 through a nitric acid ($HNO_3$) air bath 74 into flexible tubing 76 forming channel 2 of peristaltic pump 68 with the remaining extremity of tubing 76 connected to port "a" of valve 78. A regulated air source 70 having an input from air supply 17 through tube 75 is coupled through tubing 100 into a second nitric acid ($HNO_3$) air bath 102 which is coupled through tubing 103 into a sodium hypochlorite (NaOCl) air bath 104. The output of air bath 104 is connected to one extremity of flexible tubing 106 forming channel 3 of peristaltic pump 68 and with the remaining extremity of tubing 106 connected to port "c" of valve 82.

A nitric acid ($HNO_3$) reservoir 108 is connected to one extremity of flexible tubing 110, which forms channel 4 of pump 68, with the remaining extremity of tubing 110 connected to port "c" of valve 86. Flexible tubing 114, forming channel 5 of pump 68 has one extremity connected to a source 112 of double strength lauryl tryptose broth (DSLTB), with the remaining extremity connected to port "c" of valve 90. A deionized water reservoir 116, supplied by deionized water input line 15 includes an external heater 117 with a temperature controller (not shown) to elevate the temperature of the water to 100° C. Reservoir 116 is connected to one extremity of flexible tubing 118 which forms channel 6 of pump 68 with the remaining extremity connected to port "a" of solenoid operated valve 124. Port "c" of valve 124 is connected to port "a" of 4-part, solenoid-operated valve 119 with port "b" thereof connected to port "c" of valve 99. Flexible tubing 121, forming channel 7 of pump 68, connects port "d" of valve 119 to system drain 122. Similarly, port "b" of valve 124 and port "c" of valve 94 are connected to system drain 122 by means of tubings 125 and 95, respectively.

In order to measure the voltage generated within the electroanalytical cell 54 containing the growing bacteria in DSLTB 61, it is necessary to connect the combination electrode 55 of the cell to a high impedance signal conditioner 138. The type of signal conditioner used is not critical with the only requirement being that it be of the high impedance type. The signal conditioner must have an input impedance at least within the range of $10^6$ ohms to $10^8$ ohms. If a relatively low impedance signal conditioner were used, too much current would be drawn through the measuring device, thus upsetting the charge-charge interaction between the measuring electrode and the bacteria, destroying rhe electrostatic potential build-up at the measuring electrode. With the destruction of the electrostatic potential at the electrode, no potential readings could be obtained. Of course, other devices, such as an amplifier and a recording device (not shown) could also be added. All valves are shown in the normally deenergized position.

Although coliform detection apparatus 62 may be manually operated, it is to be understood that the use of an automated control is the preferred embodiment of the present invention. Thus, although no wiring interconnections are shown for simplicity, all valves are solenoid pilot operated by command signals sequentially generated in digital computer 16 and coupled into analyzing sensor assembly 14 and analyzing assembly 62 over conductor 26. It is to be further understood that the coliform detector apparatus is intended to permit independent self-contained operation when the required sources of air, water and electrical power are available. Additionally, any process control computer having the required interface characteristics which is capable of being programmed to handle the required valve operation schedules and resultant data flow can be utilized in the system of the present invention.

In operation, the interior of the electroanalytical cell must first be cleaned and sterilized prior to culturing the growth medium used in the detection process. The initial step of the clean-up begins with draining spent nutrient from the cell 54. This is accomplished by energizing solenoid pilot operated valves 99 and 119 and energizing channel 7 of peristaltic pump 68 for drawing spent nutrient in the interior of cell 54 through tubing 96, valve 99, tubing 120, valve 119 and tubing 121 and pump 68, and discharging the spent nutrient into system drain 122.

Next, valves 99 and 119 and channel 7 of pump 68 are deenergized and channel 4 of pump 68 and solenoid pilot operated valves 86 and 94 are energized to partially fill cell 54 with nitric acid from reservoir 108. Then pump channel 4 and valve 86 are denergized and pump channel 3 and valve 82 are energized to introduce an acid-treated, sodium hypochlorite (NaOCl) air wash from air tank 70 (through acid air bath 102 and NaOCl air bath 104) into the interior of cell 54 through valves 82, 86, 90, 94 and 99, causing the nitric acid within the cell to be sprayed against the inner cell surface areas of effect bacteriostat of any organisms present within the cell. Pump channel 3 and valves 99 and 119 in pump channel 7 are energized to drain the nitric acid from within the cell as above mentioned for draining spent nutrient.

With all valves deenergized as shown, regulated air from source 70 passes through a nitric acid ($HNO_3$) air bath 74, where peristaltic pump 68 draws the acid washed air from bath 74 through flexible tubing 76, with the air thereafter pumped through valve 78, tubing 80, valve 82, tubing 84, valve 86, tubing 88, valve 90, tubing 92, valve 94 and then through tubing 95 into system drain 122. At the same time, deionized water received in water reservoir 116 from water input 15 is heated to 100° C. by heater 117 and thereafter drawn from reservoir 116 through tubing 118 and pumped through solenoid-operated valve 124 into system drain 122 through tubing 125. The above steps sterilize and clean the lines and valves to cell 54.

Pump channel 6 and solenoid-operated valves 124 and 99 are then energized to fill the interior of the cell with deionized water from source 116 at an elevated temperature through valves 124, 119 and 99. Upon completion of the deionized water fill of the cell 54, pump channel 6 and valves 124 and 99 are deenergized and temperature controller 146, upon signals from computer 16, energizes heater 134, elevating the temperature of the oil bath 132 and, thus, elevating the temperature of the water within the cell to 85° C. When the preselected temperature of 85° C. is reached, as indicated by a signal output from thermistor 135 to temperature controller 146, power to heater 134 is terminated. Through use of the signal generated by thermistor 135, temperature controller 146 applies power to heater 134 to maintain the interior temperature of the cell at 85° C. for a half-hour soak period.

Following the elevated temperature soak, valves 99 and 119 in pump channel 7 are energized to drain the water from the interior of the cell in the manner above described, after which valves 99 and 119 and pump channel 7 are deenergized. Next, pump channel 5 and solenoid pilot operated valves 90 and 94 are energized to fill cell 60 with a predetermined volume of DSLTB or other suitable bacteria growth medium. Pump channel 5 and valves 90 and 94 are then deenergized and the temperature of the nutrient within the cell is elevated to 85° C. by operation of the temperature controller 146, heater 134 and thermistor 135 as above-described for the elevation of temperature of the deionized water. Again, the temperature of the growth nutrient is maintained at 85° C. for approximately one-half hour after which controller 146 is reprogrammed by digital computer 16 to provide temperature stabilization at either 35° C. or 44.5° C., dependent upon the type of coliform bacteria to be measured. Once the temperature is stabilized at the preselected temperature, pump channel 1 and solenoid-operated valves 78 and 94 are energized briefly to permit inoculation of the temperature-stabilized, growth nutirent with a preselected quantity of bacteria in the sample from source 64. Pump channel 1 and valves 78 and and 94 are then deenergized. The sterilization of valves 78, 82, 86, 90, 94, and 99 can be accomplished as above described.

Coliform bacteria contained in the sample used to innoculate the growth nutrient 61 produces molecular hydrogen during reproduction from the lactose sugar contained in the DSLTB. As the molecular hydrogen concentration evolved during reproduction of the coliform in solution increases so does the electrical potential between the measuring and reference electrodes 58 and 56, respectively.

This reaction produces approximately a 0.5—volt change from a bacteria concentration of $10^5$ cells/ml and less, to approximately $10^8$ cells/ml. Initial bacteria cell concentration is observed to be inversely proportional to length of detection time. The detection time is measured from the incubator cell 60 innoculation to a discernible change in the electrode voltage reading. As above-mentioned, the incubation soak temperature determines the coliform detected, a 35° C. soak temperature being used to detect total coliform concentrations, while a 44.5° C. soak temperaure is specific for E. coli fecal coliform determinations.

The digital computer 16, as above described, functions as a process control means to control the sequence of operation of the biosensor sub-assembly 62 in conjunction with analyzer assembly 14. The various sequential electrical signal commands from computer 16 are sent to the biosensor sub-assembly 62 and assembly 14 through command interface line 26 and receives status signals via status interface line 28, including electrical signals from signal conditioner 138 and temperature controller 146. Accordingly, the computer 16 can measure the elapsed time delay between inoculation of the growth medium and the detection of an electrical potential change in the cell as measured by signal conditioner 138 and sent to assembly 14 and computer 16 via conductor 140 and status interface line 28. The elapsed delay time is functionally related to the concentration of bacteria in the sample.

Figure 4:
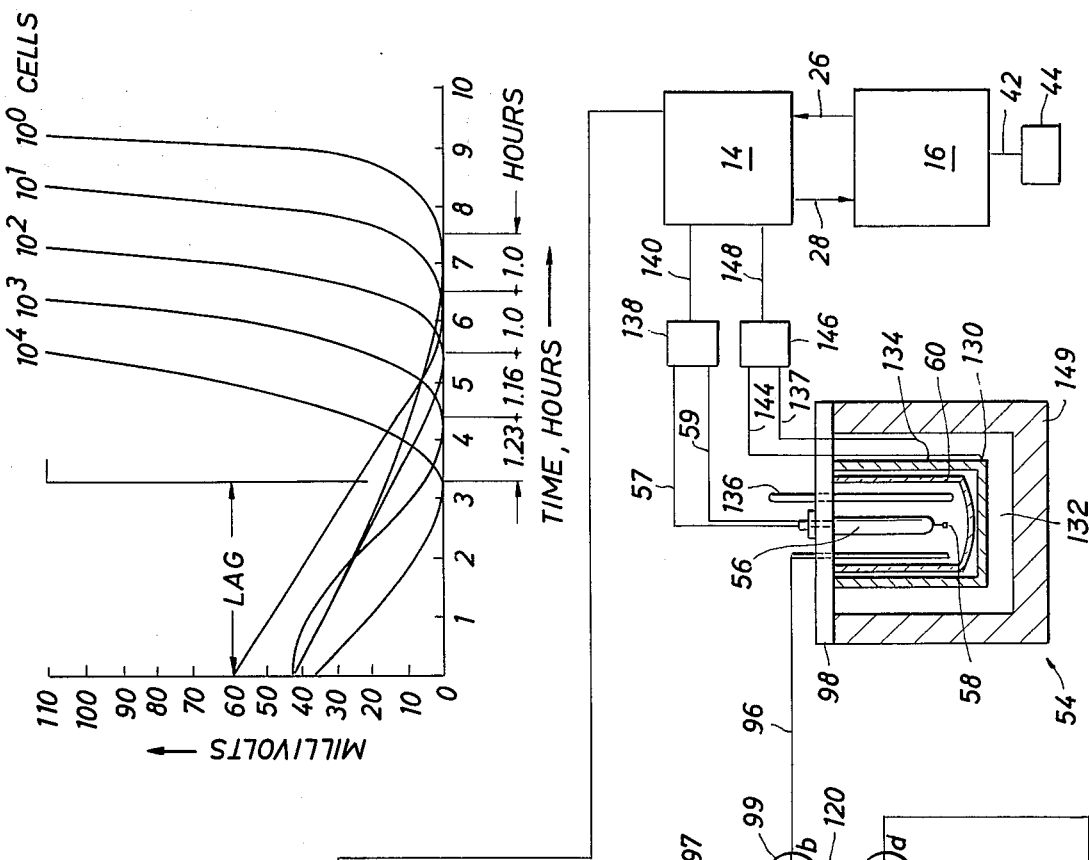
FIG. 4 is a graphical representation of electrical potential in millivolts versus time in hours for one embodiment of the present invention which illustrates the rapid hydrogen build-up for various concentrations of coliform bacteria.

Referring now to FIG. 4, a family of standard curves is shown which relates the number of coliform cells in an aqueous sample to the detection time required for the build-up of hydrogen within the growth nutrient to reach a detectable state. By comparing the measured detection time with the family of curves, the coliform concentration of the aqueous sample can be determined. The use of the digital 16 to perform the comparison simplifies the procedure.

The computer 16 determines the bacteria concentration functionally related to the measured delay time and generates an electrical signal representative thereof which is applied to display play means 44 via line 42 for conversion to a visual display or reading of the bacteria concentration.

As shown by the graphs in FIG. 4, even a sample having a high cell count per milliliter has a lag-time prior to the rapid hydrogen build-up period of several hours. As a result, the embodiment shown in FIG. 3 may require as much as twelve hours between coliform concentration determinations. When the system is used to monitor the effectiveness of a water treatment system, it is desirable that determinations be made more frequently than twice in a 24-hour period.

Figure 5:
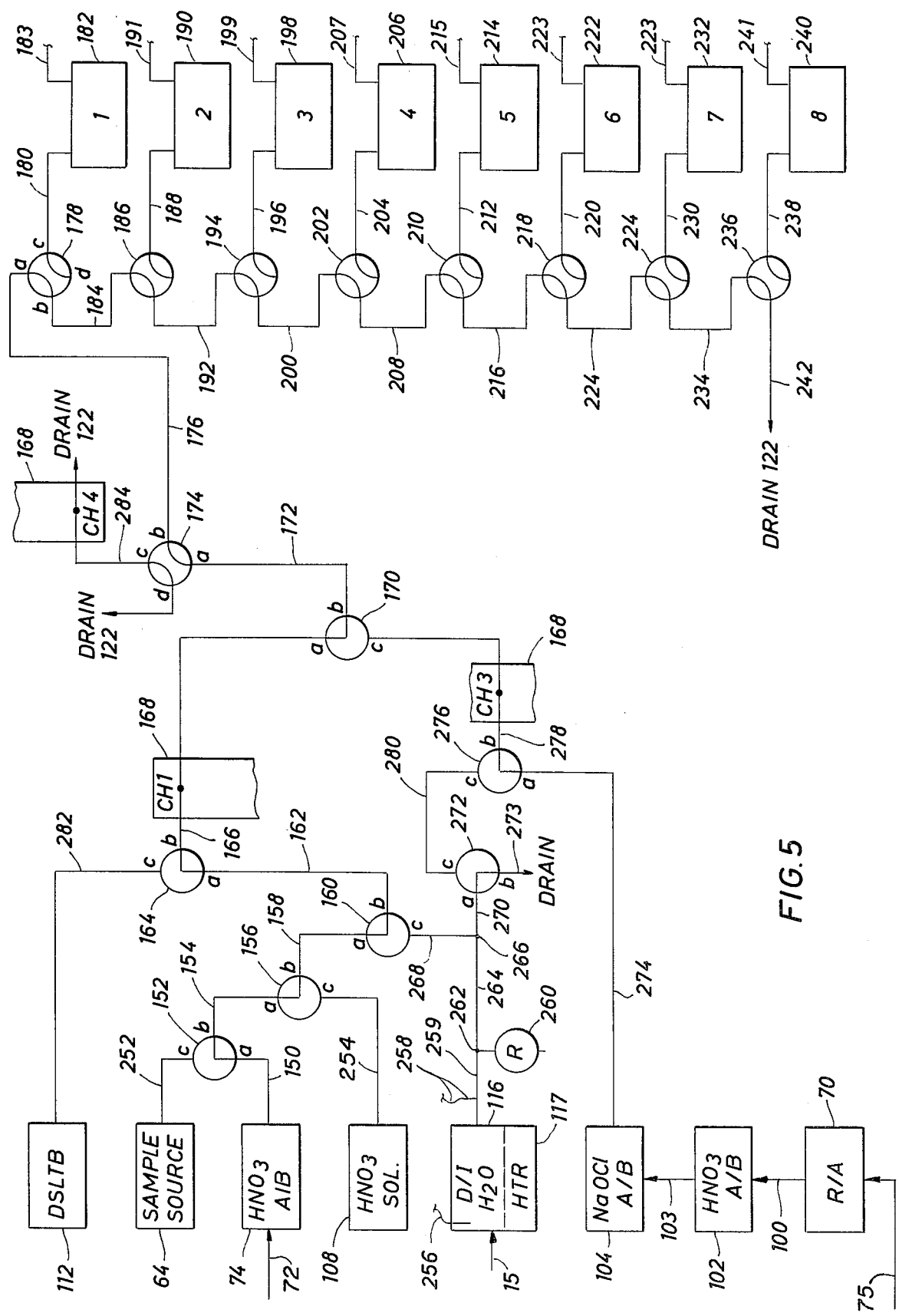
FIG. 5 is a block schematic diagram illustrating a multicell embodiment of the automated apparatus for performing the coliform detection measurement of water samples in accordance with the method and apparatus of the present invention.

Accordingly, referring now to FIG. 5, an alternative embodiment of the present invention is shown that includes a preselected number of individual analytical cells which may be sequential cleaned, sterilized and innoculated so as to reduce the lag-time between successive coliform concentration determinations.

In an alternative embodiment shown in FIG. 5, the reservoirs and sources have the same reference numbers as those shown in FIG. 3. In this embodiment, a source or supply of free air 17 is connected by tubing 72 to nitric acid air bath 74 which is connected to port "a" of a solenoid pilot operated valve 152 by tubing 150 with port "b" connected to port "a" of solenoid pilot operated valve 156 by tubing 154. Port "b" of valve 156 is connected to port "a" of solenoid pilot operated valve 160 by tubing 158 with port "b" connected by tubing 162 to port "a" of solenoid pilot operated valve 164. Port "b" of valve 156 is connected to port "a" of solenoid pilot operated valve 160 by tubing 158 with port "b" connected by tubing 162 to port "a" of solenoid pilot operated valve 164. Port "b" of solenoid pilot operated valve 164 is connected to one extremity of a flexible tubing 166 which forms channel 1 of a peristaltic pump 168, withthe other extremity connected to port "a" of solenoid pilot operated valve 170. Port "b" of valve 170 is connected by tubing 172 to port "a" of a 4-port solenoid pilot operated valve 174, with port "b" of valve 174 connected by tubing 176 to port "a" of a 4-port solenoid pilot operated valve 178. Although it would be possible to use 3-port solenoid pilot operated valves in this embodiment, four-way Teflon coated solenoid pilot operated valves are readily available, and the use of Teflon enhances the cleaning process.

Eight incubator cells 182, 190, 198, 206, 214, 222, 232 and 240 are serially connected by eight of the four-way solenoid pilot operated Teflon valves as follows: cell 182 is connected to port "c" of valve 178 by tubing 180 with port "b" of valve 178 connected by tubing 184 to port "a" of valve 186; cell 190 is connected to port "c" of valve 186 by tubing 188 with port "b" of valve 186 connected to port "a" of valve 184 by tubing 182; cell 198 is connected to port "c" of valve 194 by tubing 196 with port "b" connected to port "a" of valve 202 by tubing 200; cell 206 is connected to port "c" of valve 202 by tubing 204 with port "b" thereof connected by tubing 208 to port "a" of valve 210; cell 214 is connected by tubing 212 to port "c" of valve 210 with port "b" thereof connected by tubing 216 to port "a" of valve 218; cell 222 is connected by tubing 220 to port "c" of valve 218 with port "b" thereof connected by tubing 224 to port "a" of valve 226; cell 232 is connected by tubing 230 to port "c" of valve 226 with port "b" thereof connected by tubing 234 to port "a " valve 236; cell 240 is connected to port "c" of valve 236 by tubing 238 with port "b" connected by tubing 242 to system drain 122.

A source reservoir of the coliform bacteria sample 64 is connected to port "c" of valve 152 by tubing 252. The nitric acid ($HNO_3$) solution reservoir 108 is connected to port "c" of valve 156 by tubing 154. Deionized water reservoir 116 is shown to include a thermistor 256 extending into the interior of the reservoir and a thermometer 258 interposed in tubing 259 which provides electrical signals to a conventional controller (not shown) used to control the on-off sequences of heater 117 to maintain the temperature of the deionized water within reservoir 116 at 100° C. The free extremity of tubing 259 is connected to one extremity of tubing 264. The leg of "T" connector 262 is connected to a pressure-relief valve 260. The remaining extremity of tubing 264 is connected to the leg of a "Y" connector 266 with one arm connected by tubing 268 to port "c" of valve 160 and the remaining arm connected by tubing 270 to port "a" of valve 272. Port "b" of valve 272 is connected by tubing 273 to system drain 122.

Regulated air source 70 is connected by tubing 100 to nitric acid ($HNO_3$) air bath 102 which in turn is connected by tubing 103 to sodium hypochlorite (NaOCl) air bath 104. The output from air bath 104 is connected by tubing 274 to port "a" of solenoid pilot operated valve 276 with tubing 280 connecting port "c" of valve 276 with port "c" of valve 272. Port "b" of valve 276 is connected to one extremity of flexible tubing 278 which forms channel 3 of pump 168 with the remaining extremity connected to port "c" of valve 170. The DSLTB nutrient reservoir 112 is connected by tubing 282 to port "c" of valve 164. Port "c" of valve 174 is connected to one extremity of flexible tubing 284 which forms channel 4 of pump 168 with the remaining extremity connected to system drain 122 and with port "d" of valve 174 also connected to system drain 122.

In operation, the same process steps are utilized in the multi-cell embodiment as has been above-described for the single-cell embodiment shown in FIG. 3. Again, all solenoid-operated valves are shown in the deenergizing position. Additionally, channel 1 of peristaltic pump 168 and valve 174 are energized in order that nitric-acid-washed air from air bath 74 is continuously pumped through the system drain 122. Deionized water at an elevated temperature from reservoir 116 is allowed to flow to system drain 122 through valve 272.

As above-described, the first step in the process is to drain spent nutrient from each cell. By starting the draining process with cell 240, the spent nutrient can also be drawn from within the associated valve 236 and all tubing connections. Thus, channel 4 of peristaltic pump 168 is energized, as are solenoid pilot operated valves 174 and 236, drawing spent nutrient from cell 240 and pumping it to drain 122. After a sufficient time to enable pump channel 4 to empty cell 240 of nutrient, and to draw the nutrient in tubing 24 past solenoid pilot operated valve 226, valve 236 is deenergized and valve 226 is energized to begin nutrient drain of cell 232. The same sequence is followed to drain the remaining cells, that is, valve 218 is energized to drain cell 222, valve 210 is energized to drain cell 214, valve 202 is energized to drain cell 206, valve 194 is energized to drain cell 148, valve 186 is energized to drain cell 190, and valve 178 is energized to drain cell 182, with the various valves being deenergized and energized in a timed sequence to insure that the spent nutrient drawn from within each cell is drawn past the valve which is next in sequence to be energized. During the period that the cells are being drained of nutrient, channel 1 of pump 168 and solenoid pilot operated valve 156 are energized to pump 0.1 NHNO$_3$ into the system to effect bacteriostat on the system valves 156, 160, 164 and 170 and associated tubing. The nitric acid solution is ultimately pumped through ports "a"–"d" of valve 174 to drain 122.

The next process step is to inject equal volumes of 0.1 NHNO$_3$, which is now available in the system lines as a result for performing the above-described bacteriostat thereon into each cell. Channel 1 of pump 168 and valve 156 remain energized, and valve 236 is again energized to begin the cell fill with cell 240. In order to completely fill the tubing between valve 174 and valve 236, the fill time for cell 240 exceeds the other cell fill times by one minute to allow the nitric acid to travel in through the main line between valves 174 and 236. Again, as above-described for the nutrient drain from each cell, the valve associated with each cell is sequentially energized and deenergized in the proper order and for the preselected time period to inject a predetermined volume of nitric acid into each cell, beginning with valve 236 and cell 240 and ending with valve 178 and cell 182.

After cell 182 has been filled with the predetermined volume of HNO$_3$, valves 156 and 236 are deenergized to permit acid washed air from nitric acid air bath 74 to clear the system lines of nitric acid. When line 242 is completely free of nitric acid, channel 3 of pump 168 and solenoid pilot operated valve 170 is energized to permit acid-treated, NaOCl washed air to flow through the system lines. Next, the cell valves are energized sequentially beginning with valve 178 for cell 182, to flow the NaOCl washed air into each cell in turn for spraying the nitric acid solution therein against the cell surface area to affect bacteriostat of any organisms present therein. Each cell in turn is air washed with the nitric acid until bacteriostat spraying of cell 240 is completed, at which time channel 3 and valves 170 and 236 are deenergized.

Upon completion of the nitric acid air-wash of each cell, channel 4 of pump 168 and valve 174 are energized with the corresponding cell valves being energized sequentially starting with cell 182 and valve 178 to drain the nitric acid from within each cell. The drain times are equal with cell 182 being drained first. Again, channel 1 of pump 168 and valve 156 are energized to perform the bacteriostat operation on the system lines.

Each cell 182, 190, 198, 206, 214, 222, 232 and 240 are configured as above-depicted in FIGS. 2 and 3. However, for simplicity, conductors 57, 59, 137 and 144, which connect to the high impedance signal conditioner 138 and temperature controller 146, respectively, are shown as a cable bundle, with cable 183 associated with cell 182, cable 191 associated with cell 190, cable 199 associated with cell 198, cable 207 associated with cell 206, cable 215 associated with cell 214, cable 223 associated with cell 222, cable 233 associated with cell 232, and cable 241 associated with cell 240.

The next process step, as has been described, requires that the oil bath 132 associated with each cell be preheated to 85° C. Once the oil bath of a cell reaches the 85° C. temperature, in the manner above-described for the single cell embodiment, it is then flushed with a predetermined quantity of deionized water from reservoir 116 by energizing channel 1 of pump 168 and valve 160, with valve 236 being energized to effect the flush of cell 240 first. Again, as has been above-described, each cell valve is sequentially energized in its turn, and thereafter deenergized, permitting the predetermined quantity of deionized water at the elevated temperature to be flowed into each cell. When each cell has received the predetermined quantity of deionized water, the temperature is stabilized at 85° C. and each cell is maintained at that temperature to perform a hot water soak on the interior of the cell for approximately one-half hour.

Next, the drain sequence is initiated to discharge the deionized water from the interior of the cells by again energizing channel 4 of pump 168 and valve 174 with valve 236 being energized first to accomplish the drain of the cells and accompanying valve and lines. During the water drain of each cell, channel 1 of pump 168 is energized to flow acid washed air from air bath 74 through the system and through ports "a" and "d" of valve 174 to system drain 122. Upon completion of the water drain of the cells, pump channel 3 and valves 174 and 178 are deenergized and pump channel 1 and valve 164 are energized to begin filling the cell and main lines with DSLTB bacteria growth nutrient. When the main line is full of nutrient, each cell, beginning with cell 240, is filled with a predetermined amount of the growth nutrient through sequencing of the appropriate valves as has been above described. Thereafter, the temperature of the cells is stabilized at 85° C. for the reasons above-mentioned to begin a one-half hour heat soak of the nutrient. During this time, the main line is drained of nutrient by deenergizing all valves and energizing channel 1 of pump 168 to utilize the acid-washed air to force the nutrient from the main line and valves. Once the tubing and valves are cleared, the valves are sequenced to permit draining the nutrient in each cell valve-to-cell connection tubing into the cell, beginning by energizing valve 236 to drain line 238 into cell 240. Similarly, the appropriate valves are sequentially energized and thereafter deenergized to effect the drain of line 230 into cell 232, line 220 into cell 222, line 212 into cell 214, line 204 into cell 206, line 196 into cell 198, line 188 into cell 190, and line 180 into cell 182.

Upon completion of the one-half hour 85° C. heat soak of the nutrient, a temperature controller (see 146 in FIG. 3) receives signals from the digital computer 16 to reestablish the preselected incubation temperature of either 35° C. for total coliform concentration detection or of 44.5° C. for only fecal coliform concentration detection. During the time the preselected incubation temperature is being established in the cells, channel 1 and valve 152 are energized to fill the lines with an aqueous sample from sample source 64. Next, the cell valves are sequentially sequenced on and then off to inject a predetermined quantity of the sample into each tubing connecting the cell valve with its respective cell. Thereafter, valve 152 is deenergized while channel 1 pumps acid washed air through the system to clear the lines of the aqueous sample. The inoculation of the nutrient is achieved by energizing channel 1 to flow acid washed air through the system and energizing channel 1 and sequencing the cell valve to inject the sample contained within the cell-tubing into the associated cell.

Once the nutrient in each cell has been inoculated with the sample, the process above-described for the single cell embodiment is followed for each separate cell in the multi-cell embodiment. Thus after a lag-time of several hours, the bacteria growth will be such that the metabolically induced hydrogen will create a potential difference of sufficient magnitude to be measured by the measuring and reference electrodes 58 and 56, respectively (see FIGS. 2 and 3). The time-duration period will then be compared with the standard set of curves shown in FIG. 4 to determine the coliform bacteria concentration in the aqueous sample.

The above-described sequence for process steps have been directed to an initial start-up of the system. It may be desirable, in order to reduce the time between concentration determinations to set up a schedule by which each cell in turn is cleaned, sterilized, innoculated, incubated and concentration determined. It may be further desirable to configure some of the cells to detect the total coliform bacteria concentration and the others to detect the fecal coliform bacteria concentration. Thus, it may be seen that the present embodiment provides a system and process for periodically and rapidly determining the concentration of coliform bacteria in an aqueous sample.

Although specific embodiments have been described in detail hereinbefore, it is understood that the subject invention is not limited thereto and all variations and modifications thereof are contemplated and are included within the spirit and scope of the invention as defined by the appended claims.

What is claimed is:

1. A method of continuous determination of the concentration of bacteria contained in a selected fluid, comprising the steps of:

providing a liquid growth medium at selected intervals, controlling the environment of said liquid growth medium by maintaining the temperature of said medium at a first preselected temperature of 85° C. for a preselected heat-soak time period of approximately 30 minutes, inoculating said liquid growth medium with a predetermined quantity of the selected fluid containing the bacteria, culturing the bacteria contained in said selected fluid in said liquid growth medium for evolving hydrogen metabolically produced by the growth of the bacteria by maintaining the temperature of said inoculated growth medium at a second preselected temperature of either 35° C. or 44.5° C., detecting a change in potential between a measuring electrode and a reference electrode in contact with said bacteria and liquid growth medium as a result of said evolving hydrogen, generating an electrical signal representative of said change in potential, measuring the period of time between said inoculating of said of said liquid growth medium with the bacteria and said detecting a change in potential between said electrodes, determining the concentration of the bacteria in said inoculated liquid growth medium as a function of said measured period of time, discharging said liquid growth medium containing said cultured bacteria subsequent to said measuring and determining steps, initiating a cleaning and steriling cycle for removing bacterial residue remaining after discharging said liquid growth medium containing said cultured bacteria, and reinitiating said above steps beginning with providing a liquid growth medium.

2. An automated bacteria concentration measuring apparatus, comprising an aqueous sample source containing the bacteria, a source of a nutrient growth medium for promoting bacteria growth, an electroanalytical incubator cell means adapted to receive said nutrient growth medium and said aqueous sample containing the bacteria, said cell having disposed therein a reference electrode and a measuring electrode for measuring a charge of electrical potential within said cell, process control means for providing electrical control signals to control the sequence of operation of the concentration measuring apparatus, charging means communicating with said source of nutrient growth medium and said cell means for charging said cell means with a selected quantity of said medium in response to electrical command signals from said process control means, pumping means communicating with said aqueous sample source and said cell means for pumping a selected quantity of said aqueous sample containing said bacteria into said cell means to inoculate said nutrient growth medium in response to electrical command signals from said process control means, sterilizing means communicating with said cell means, said charging means and said pumping means for cleaning and sterilizing said cell means and at least a portion of said charging and pumping means prior to charging said cell means with said growth medium and inoculating said medium with said bacteria in said aqueous sample in response to command signals from said process control means, temperature control means cooperating with said cell means and said process control means for heating and maintaining said cell means at a preselected temperature in response to command signals from said process control means, a signal conditioner connected to said electrodes of said cell means for measuring the electrical potential change between said electrodes in response to the quantity of metabolic hydrogen produced by growth of said bacteria in said growth medium, said electrical potential change being functionally related to the concentration of said bacteria and said potentiometer generating an electrical signal representative of said change in electrical potential for application to said process control means, said process control means receiving said electrical signals from said signal conditioner for measuring the elapsed time from the inoculation of said growth medium with said bacteria to the detection of an electrical potential change between said electrodes by said potentiometer, said elapsed time period being functionally related to the concentration of said bacteria, said process control means determining the concentration of said bacteria functionally related to said elapsed time period and generating electrical signals representative thereof, and thereafter sending command signals to said sterilizing means to clean and sterilize said cell means preparatory to initiating another measurement cycle, and display means receiving said electrical signals from said electrical signals from said process control means representative of said bacteria concentration for connecting said signals to a visual representation of said bacteria concentration.

3. The apparatus described in claim 2, wherein said nutrient growth medium is a lactose-containing nutrient broth.

4. The apparatus described in claim 3, wherein said lactose-containing nutrient broth is double strength lauryl tryptose broth.

5. The apparatus described in claim 2, wherein said process control means is a digital computer.

6. The apparatus described in claim 2, wherein said charging means comprises,
  valve means communicating with said cell means and responsive to command signals from said process control means, and
  a peristaltic pump connecting said source of nutrient growth medium and said valve means for pumping a preselected quantity of said growth medium through said valve means into said cell means in response to said command signals from said process control means.

7. The apparatus described in claim 2, wherein said pumping means comprises,
  valve means communicating with said cell means and responsive to command signals from said process control means, and
  a peristaltic pump connecting said aqueous sample source and said valve means for pumping a preselected quantity of said aqueous sample containing said bacteria through said valve means into said cell means in response to said command signals from said process control means.

8. The apparatus described in claim 2, wherein said sterilizing means comprises,
  a source of free air,
  a first acid bath communicating with said source of free air for admitting said free air and discharging said air as acid washed air,
  a source of compressed air,
  a second acid bath communicating with said source of compressed air for admitting said compressed air and discharging said air as acid washed air,
  a sodium hypochlorite bath connected to said second acid bath for receiving said acid washed air and discharging said air as acid-sodium hypochlorite washed air,
  a source of nitric acid,
  a source of deionized water,
  heating means cooperating with said deionized water source and maintaining said water at 100° C.,
  first transfer means responsive to command signals from said process control means for interconnecting said incubator cell means containing said cultured bacteria in said nutrient growth medium with said drain for removing said cultured growth medium,
  second transfer means responsive to command signals from said process control means for sequentially interconnecting
    said source of nitric acid with said incubator cell means and transferring a selected volume of nitric acid into said cell means, and
    said sodium hyperchlorite bath with said sodium hypochlorite filled cell means for injecting a selected volume of acid-sodium hypochlorite air into said cell means to cause turbulence in said nitric acid therein for performing a bacteriostat of said cell means,
  said first transfer means responsive to command signals from said process control means for interconnecting said cell means and said drain and removing said nitric acid from said cell means to said drain after said bacteriostat of said cell means,
  third transfer means cooperating with said first and second transfer means and responsive to command signals from said process control means for interconnecting said first acid bath and at least a portion of said first and second transfer means and said system drain for admitting acid washed air into said at least a portion of said first and second transfer means for removing nitric acid therefrom to said system drain and simultaneously sterilizing said at least a portion of said first and second transfer means, and
  fourth transfer means responsive to command signals from said process control means for interconnecting said source of heated deionized water and said incubator cell means and filling said cell means with said heated deionized water and maintaining said water in said cell means for a predetermined heat soak period, and
  said first transfer means responsive to said command signals from said process control means for removing said water from said cell means and discharging said water to said system drain.

9. The apparatus as described in claim 8, wherein said acid in said first and second acid baths is nitric acid.

10. The apparatus as described in claim 2, wherein said electroanalytical incubator cell means comprises,
  an incubator cell,
  a reference electrode and a measuring electrode disposed in said cell for contact with said growth medium and said bacteria when said cell has been charged with said growth medium and innoculated with said bacteria, said electrodes interconnected to said potentiometer, sealing means for leak-tight sealing said cell with at least a portion of said electrodes projecting into the interior of said cell, and inlet means communicating with the interior of said sealed cell and cooperating with said charging means, said pumping means and said sterilizing means for permitting access to the interior of said sealed cell during said charging, inoculating and sterilizing functions.

11. The apparatus as described in claim 10, wherein said temperature control means comprises, a metal housing surrounding said incubator cell and spaced therefrom, an oil bath disposed in said space between said incubator cell and said metal housing, a heating element bonded to said metal housing on a surface opposite said oil bath for heating said oil bath and transfer of said heat from said oil bath to said incubator cell, a temperature measuring means connected to said heating element for measuring the temperature thereof, said temperature measuring means generating an electrical signal representative of said measured temperature, control circuit means connecting said heating element and said temperature measuring means for receiving said electrical signals representative of said measured temperature and responsive to command signals from said process control means, controlling the heat generated by said heating element for elevating and maintaining the temperature of said growth medium in said cell at a predetermined temperature.

* * * * *